(12) United States Patent
Rongione

(10) Patent No.: US 10,961,483 B2
(45) Date of Patent: Mar. 30, 2021

(54) METHOD FOR PREPARING 2-MONOACYLGLYCERIDES

(71) Applicant: STEPAN COMPANY, Northfield, IL (US)

(72) Inventor: Joseph C. Rongione, Middletown, NJ (US)

(73) Assignee: STEPAN COMPANY, Northfield, IL (US)

( * ) Notice: Subject to any disclaimer, the term of this patent is extended or adjusted under 35 U.S.C. 154(b) by 0 days.

(21) Appl. No.: 15/740,224

(22) PCT Filed: Jun. 28, 2016

(86) PCT No.: PCT/US2016/039728
§ 371 (c)(1),
(2) Date: Dec. 27, 2017

(87) PCT Pub. No.: WO2017/003992
PCT Pub. Date: Jan. 5, 2017

(65) Prior Publication Data
US 2018/0187125 A1    Jul. 5, 2018

Related U.S. Application Data

(60) Provisional application No. 62/188,287, filed on Jul. 2, 2015.

(51) Int. Cl.
| | | |
|---|---|---|
| *C12P 7/64* | (2006.01) | |
| *C11C 1/04* | (2006.01) | |
| *C11C 1/10* | (2006.01) | |
| *C11C 1/08* | (2006.01) | |
| *C12N 9/20* | (2006.01) | |
| *C07C 31/08* | (2006.01) | |
| *C07C 47/54* | (2006.01) | |
| *C07C 47/548* | (2006.01) | |
| *C07C 47/58* | (2006.01) | |

(52) U.S. Cl.
CPC ............... *C11C 1/045* (2013.01); *C11C 1/08* (2013.01); *C11C 1/10* (2013.01); *C12N 9/20* (2013.01); *C12P 7/6445* (2013.01); *C12P 7/6472* (2013.01); *C07C 31/08* (2013.01); *C07C 47/54* (2013.01); *C07C 47/548* (2013.01); *C07C 47/58* (2013.01); *C12Y 301/01003* (2013.01)

(58) Field of Classification Search
None
See application file for complete search history.

(56) References Cited

U.S. PATENT DOCUMENTS

| | | |
|---|---|---|
| 2,251,693 A | 8/1941 | Richardson et al. |
| 2,619,493 A | 11/1952 | Norris |
| 5,116,745 A | 5/1992 | Mazur et al. |
| 5,935,828 A | 8/1999 | Zaks et al. |
| 6,153,773 A | 11/2000 | Kolstad et al. |
| 6,537,787 B1 | 3/2003 | Breton |
| 9,034,917 B2 | 5/2015 | Bistrian et al. |
| 2007/0077214 A1* | 4/2007 | Laszlo ............... A61K 8/375 424/59 |
| 2013/0109753 A1* | 5/2013 | Bistrian ............... A61K 31/202 514/560 |
| 2013/0331588 A1 | 12/2013 | Hietsch et al. |

OTHER PUBLICATIONS

B.B. Bahule et al. "Protection of Diol as Acetonide Using Acetone and Cation Exchange Resin as a Catalyst", IOSR Journal of Applied Chenistry 3(1): 28-29 (Year: 2012).*
P. Wuts. "Greene's Protective Groups in Organic Synthesis" Chapter 3, "Protection for 1,2- and 1,3-Diols", John Wiley & Sons (Year: 2014).*
L.E. Nadjer. "Thin Film Evaporation", Ind. Eng. Chem., 56(2): 26-30 (Year: 1964).*
A. Rodriguez et al. "Synthesis of 2-monoacylglycerols and structured triacylglycerols rich in polyunsaturated fatty acids by enzyme catalyzed reactions", Enzyme and Microbial Technology 51: 148-155. (Year: 2012).*
Jérôme et al., Green Chem. 6 (2004) 72, abstract.
Yang et al., J. Agric. Food Chem. 53 (2005) 1475, abstract.
Mu et al., Prog. Lipid Res. 43 (2004) 105, abstract.
Irimescu et al., J. Am. Oil Chem. Soc. 78 (2001) 285.
Wongsakul et al., Eur. J. Lipid Sci. Technol. 105 (2003) 68, abstract.
Piantadosi et al., J. Am. Chem. Soc. 80 (1958) 6613.
Gras et al., Synlett (1999) 1835, abstract.
Yue et al., Lipids 41 (2006) 301.
Watanabe et al., J. Am. Oil Chem. Soc. 91 (2014) 1323.
Compton et al., J. Am. Oil Chem. Soc. 84 (2007) 343.
Cruz-Hernandez et al., Nutrients 4 (2012) 1781.
Muñío et al., Process Biochem. 43 (2008) 1033.
Pfeffer et al., Lipids 42 (2007) 947.

(Continued)

*Primary Examiner* — Rebecca E Prouty
(74) *Attorney, Agent, or Firm* — Dilworth IP LLC

(57) ABSTRACT

Methods for preparing and purifying 2-monoacylglyceride compounds are disclosed. In one method, an unsaturated triglyceride is reacted with water, a $C_1$-$C_8$ alcohol, or a mixture thereof in the presence of a lipase to produce a mixture comprising a 1,3-dihydroxy-2-monoacylglyceride and fatty esters or acids. Reaction of the 1,3-dihydroxy-2-monoacylglyceride with an aldehyde or ketone gives a mixture comprising a 2-monoacylglyceride acetal or ketal. Fatty esters or acids are removed from the mixture as an overhead product by distillation or wiped-film evaporation to isolate a purified 2-monoacylglyceride acetal or ketal. The inventive methods provide a 2-monoacylglyceride protected at the 1- and 3-positions such that the acyl unit remains at the 2-position. The products are enriched in unsaturated fatty acid content when compared with the unsaturated fatty acid content of the original unsaturated triglyceride. Each method utilizes a practical purification scheme that avoids the scale-up or toxicity issues of commonly employed purification strategies.

11 Claims, No Drawings

(56) References Cited

OTHER PUBLICATIONS

Bayon et al., Bioorg. Med. Chem. Lett. 6 (1996) 345.
Itabaiana Jr., et al., J. Flow Chem. 3 (2013), published online Sep. 26, 2013.
Mattson et al., J. Lipid Res. 9 (1968) 79.
PCT International Search Report dated Sep. 21, 2016 from corresponding Application No. PCT/US2016/039728, 3 pages.

* cited by examiner

METHOD FOR PREPARING 2-MONOACYLGLYCERIDES

FIELD OF THE INVENTION

The invention relates to protected 2-monoacylglyceride compositions and methods for their preparation and purification.

BACKGROUND OF THE INVENTION

Monoglyceride synthesis has long been a subject of study (see, e.g., U.S. Pat. Nos. 2,251,693; 2,619,493; and 6,153,773). Most of the work has centered on producing a random distribution of the acyl moiety (see, e.g., U.S. Pat. No. 2,619,493 and Jérôme et al., *Green Chem.* 6 (2004) 72). Predominantly, these species have been produced by the glycerolysis of triglycerides containing the desired fatty acid residues (see, e.g., Yang et al., *J. Agric. Food Chem.* 53 (2005) 1475).

Fatty acid distribution in triglycerides influences absorption, distribution, and tissue uptake (see, e.g., Mu et al., *Prog. Lipid Res.* 43 (2004) 105). Fish oil is a natural source of polyunsaturated fatty acids (PUFA) such as docosahexaenoic acid (DHA) and eicosapentaenoic acid (EPA). The PUFAs in these marine oils are believed to reduce the risk of coronary disease and certain cancers and to promote improved immune function.

Polyunsaturated fatty acids in fish oil are enriched at the 2-position relative to the overall fatty acid distribution (see, e.g., Irimescu et al. *J. Am. Oil Chem. Soc.* 78 (2001) 285). The synthetic routes employed by Irimescu are typical of known routes that produce symmetrically structured triacylglycerols rich in DHA and EPA with a short-chain fatty acid at the 1- and 3-positions. The methods require two enzymatic steps (cleavage of the 1- and 3-acyl groups and re-esterification at these sites with ethyl caprylate). Also, the groups on the terminal positions are still fatty acids. Ideally, the fatty acid content of the delivery system for the polyunsaturated fatty acid would be reduced compared with that of the oil source, as this consideration is important for a reduced-fat diet.

Synthetic methods that lead directly to 2-monoacylglycerides of polyunsaturated fatty acids are known. Representative examples are provided by Wongsakul et al. (*Eur. J. Lipid Sci. Technol.* 105 (2003) 68) and U.S. Pat. No. 5,116,745). Wongsakul generated 2-monoacylglycerides of a number of oils in methyl tert-butyl ether using a variety of enzymes. 2-Monoacylglycerides enriched in DHA and EPA are produced by this type of process, but the process requires a solvent, has relatively long reaction times, and provides no protecting groups at the 1- and 3-positions. In the '745 patent, a two-phase system (a buffered aqueous phase and an oil phase) is used to produce 2-monoacylglycerides of vegetable oils, followed by reaction of the product with an acid anhydride stream rich in DHA. This method suffers from poor reactor efficiency and the need to recover the product at $-78°$ C., an impractical temperature for large-scale processes. The same deficiencies can be found in the process of U.S. Pat. No. 5,935,828. In all of these examples, migration of the acyl group from the 2-position to the unprotected terminal hydroxy groups can be expected.

U.S. Pat. No. 2,619,493, Piantadosi et al. (*J. Am. Chem. Soc.* 80 (1958) 6613), and Gras et al. (*Synlett* (1999) 1835) describe processes of interest. In each of the former two processes, production of the glycerol acetals is nonspecific, i.e., in each process, both the 1,2- and 1,3-cyclic isomers are produced. Because the 1,2-benzylidene glycerol acetal predominates, this is not an efficient method to generate high purity 2-monoacylglycerides from polyunsaturated fatty acids. Improvements in generating a high-purity 1,3-benzylidene glycerol acetal allowed Gras et al. to produce symmetric triglycerides via an acetal-protected 2-monoacylglyceride. This route suffers from corrosive reactants and the need for a second process to refine the desired PUFA stream prior to transesterification with 1,3-benzylidene glycerol acetal. Preferably, the acid stream would not require enrichment prior to use in forming the protected 2-monoacylglyceride. Any process that uses a preformed glycerol acetal or ketal suffers this shortcoming.

Other non-fatty acid groups could be used to block the 1- and 3-positions of glycerol. Yue et al. (*Lipids* 41 (2006) 301) showed that the terminal positions of glycerol could be protected with ether linkages, in this case a 1,3-dibenzyl glycerol. The 2-position was esterified with an acyl chloride. The ether protecting groups were removed via hydrogenation. However, this route has several drawbacks. Synthesis of 1,3-dibenzyl glycerol employs several toxic compounds, notably epichlorohydrin. The esterification with acyl chlorides generates hydrogen chloride, a side product that requires significant engineering controls to manage. Lastly, catalytic cleavage of the ether linkages takes place under conditions that favor migration of the acyl group from the 2-position to one of the terminal hydroxyl groups.

Watanabe et al. (*J. Am. Oil Chem. Soc.* 91 (2014) 1323) describe an enzymatic analysis of positional distribution of fatty acids in solid fat by 1,3-selective transesterification with a lipase. The authors observed, consistent with earlier investigations, that a variety of reaction conditions promote migration of acyl moieties from the 2-position to the 1- or 3-position. A proton NMR study by Compton et al. (*J. Am. Oil Chem. Soc.* 84 (2007) 343) provided dramatic evidence (see FIG. 2, p. 345) of how rapidly an unprotected 2-monoacylglyceride will isomerize to a 1-monoacylglyceride at only $60°$ C.

Cruz-Hernandez et al. (*Nutrients* 4 (2012) 1781) describe benefits of structured and free monoacylglycerides for delivery of EPA to tissues in individuals having lipid malabsorption conditions (see also U.S. Pat. No. 9,034,917). To stabilize the 2-monoacylglycerides, these materials were used in protected form, either as the 1,3-diacetate or as the vanillin acetal. These products were used as received from Stepan Company, so details of how they were made or purified are not disclosed.

Isolation and purification of 2-monoacylglycerides is another important consideration. When the 2-monoacylglyceride is unprotected, many isolation methods will promote migration of the acyl group to the 1- or 3-position, particularly if heating is involved. Whether or not the 1- and 3-positions are protected, the most common ways to isolate and purify these materials typically involve solvent extraction, column chromatography, crystallization, or some combination of these (see, e.g., M. Muñío et al., *Process Biochem.* 43 (2008) 1033; Irimescu et al. *J. Am. Oil Chem. Soc.* 78 (2001) 285; Watanabe et al., *J. Am. Oil Chem. Soc.* 91 (2014) 1323; or Pfeffer et al. *Lipids* 42 (2007) 947). While many of these techniques are practical for lab-scale work with gram or milligram quantities, they can be unworkable on an industrial scale. Moreover, some of the purification methods rely on chemicals that cannot be tolerated in foods, drugs, dietary supplements, or other products intended for human consumption.

Improved methods for making and isolating 2-monoacylglycerides are needed. In particular, the industry would benefit from improved ways to produce and purify protected 2-monoacylglycerides. Ideally, both the synthesis and purification routine would be practical to implement industrially and would provide products suitable for human consumption.

SUMMARY OF THE INVENTION

In one aspect, the invention relates to a method for preparing and purifying a 2-monoacylglyceride acetal or ketal. The method comprises three steps. An unsaturated triglyceride is first reacted with at least two molar equivalents of water, a $C_1$-$C_8$ alcohol, or a mixture thereof in the presence of a lipase at a temperature within the range of 20° C. to 80° C. for a time sufficient to produce a reaction mixture comprising a 1,3-dihydroxy-2-monoacylglyceride and fatty esters or acids. The 1,3-dihydroxy-2-monoacylglyceride is then reacted with at least one molar equivalent of an aldehyde or ketone, optionally in the presence of an acid catalyst, to produce a mixture comprising a 2-monoacylglyceride acetal or ketal. Next, the fatty esters or acids are removed from the mixture as an overhead product by distillation or wiped-film evaporation to isolate a purified 2-monoacylglyceride acetal or ketal. Preferably, the 2-monoacylglyceride acetal or ketal is further purified by distillation to separate it from less-volatile impurities.

In another aspect, an unsaturated triglyceride is reacted with at least two molar equivalents of a lower alkyl ester or carboxylic acid in the presence of a lipase at a temperature within the range of 20° C. to 80° C. for a time sufficient to produce a reaction mixture comprising a 1,3-dicarboxy-2-monoacylglyceride and fatty esters or acids. Thereafter, fatty esters or acids are removed from the mixture as an overhead product by distillation or wiped-film evaporation to isolate a purified 1,3-dicarboxy-2-monoacylglyceride. Preferably, the 1,3-dicarboxy-2-monoacylglyceride is further purified by distillation to separate it from less-volatile impurities.

Each method provides a 2-monoacylglyceride protected at the 1- and 3-positions such that the acyl unit remains at the 2-position. Each method provides a product that is enriched in unsaturated fatty acid content when compared with the unsaturated fatty acid content of the original unsaturated triglyceride. The product can therefore provide a desirable unsaturated fatty acid without also delivering additional fatty acid components. Each method utilizes a purification scheme that is practical to implement industrially, thereby avoiding scale-up or toxicity issues of commonly employed purification strategies such as column chromatography, crystallization, or solvent extraction.

DETAILED DESCRIPTION OF THE INVENTION

I. Preparation and Purification of 2-monoacylglyceride Acetals or Ketals

In a first aspect, the invention relates to a method of preparing and purifying a 2-monoacylglyceride acetal or ketal. The method comprises three steps. First, an unsaturated triglyceride is reacted with water, a $C_1$-$C_8$ alcohol, or a mixture thereof. The reaction is performed in the presence of a lipase under conditions effective to produce a mixture comprising a 1,3-dihydroxy-2-monoacylglyceride and fatty esters or acids. The 1,3-dihydroxy-2-monoacylglyceride is then reacted with at least one molar equivalent of an aldehyde or ketone, optionally in the presence of an acid catalyst, to produce a mixture comprising a 2-monoacylglyceride acetal or ketal. Next, the fatty esters or acids are removed from the mixture as an overhead product by distillation or wiped-film evaporation to isolate a purified 2-monoacylglyceride acetal or ketal.

A. Conversion to a 1,3-dihydroxy-2-monoacylglyceride

Unsaturated triglycerides suitable for use are well known, and many occur naturally. In general, they are usually oils obtained from vegetable or animal sources. Preferred unsaturated triglycerides have residues of polyunsaturated fatty acids, particularly at the 2-position of the triglyceride. In some aspects, the polyunsaturated fatty acid is an omega-3 or omega-6 polyunsaturated fatty acid. One class of suitable polyunsaturated fatty acids has one or more "methylene-interrupted" polyene units, where two carbon-carbon double bonds are separated by a methylene (—$CH_2$—) group, and the carbon-carbon double bonds are primarily or exclusively in a cis-configuration. The omega-3 fatty acids are preferably $C_{16}$ to $C_{24}$ acids.

Thus, suitable unsaturated triglycerides can incorporate units from these methylene-interrupted "n3" acids: hexadecatrienoic acid (16:3, "HTA"); alpha-linolenic acid (18:3, "ALA"); stearidonic acid (18:4 "SDA"); eicosatrienoic acid (20:3, "ETE"); eicosatetraenoic acid (20:4, "ETA"); eicosapentaenoic acid (20:5, "EPA"); heneicosapentaenoic acid (21:5, "HPA"); docosapentaenoic acid (22:5, "DPA"); docosahexaenoic acid (22:6, "DHA"); tetracosapentaenoic acid (24:5); and tetracosahexaenoic acid (24:6).

Suitable unsaturated triglycerides can incorporate units from these methylene-interrupted "n6" acids: linoleic acid (18:2); gamma-linolenic acid (18:3); eicosadienoic acid (20:2); dihomo-gamma-linolenic acid (20:3); arachidonic acid (20:4, "ARA"); docosadienoic acid (22:2); adrenic acid (22:4); docosapentaenoic acid (22:5); tetracosatetraenoic acid (24:4); and tetracosapentaenoic acid (24:5).

Unsaturated triglycerides that incorporate a high proportion of omega-3 unsaturated fatty acids are preferred. Particularly preferred unsaturated triglycerides are fish oils, which tend to be high in polyunsaturated fatty acids, particularly ARA, EPA, and DHA.

The unsaturated triglyceride is reacted with at least two molar equivalents of water, a $C_1$-$C_8$ alcohol, or a mixture thereof. Suitable alcohols include methanol, ethanol, 1-propanol, 2-propanol, 1-butanol, 2-butanol, tert-butyl alcohol, 1-hexanol, 1-octanol, and the like, and combinations thereof. Ethanol is particularly preferred. A large excess of water or the alcohol can be used. A preferred range is from 2 to 50 molar equivalents, more preferably from 2 to 10 molar equivalents.

The reaction is performed in the presence of a lipase, preferably a 1,3-specific lipase, which catalyzes conversion of the unsaturated triglyceride to a 1,3-dihydroxy-2-monoacylglyceride. Suitable lipases are conveniently isolated from fungi, yeasts, and other microorganisms. For instance, the lipase can be obtained from *Candida antarctica, Candida rugosa, Thermomyces lanuginosus, Rhizopus delemar, Rhizomucor miehei*, and combinations thereof. Preferred lipases are obtained from *Candida antarctica, Thermomyces lanuginosus*, and *Rhizomucor miehei*. A "1,3-specific" lipase can selectively cleave fatty acids from the 1- and 3-positions of a triglyceride while leaving the fatty acid residue at the 2-position intact. Suitable 1,3-specific lipases can be obtained commercially from Novozymes, Sekisui Enzymes, Calzyme Laboratories, and other suppliers. Examples include the Lipozyme® and Novozym® products of Novozymes, such as Lipozyme® TL IM and Lipozyme® RM IM.

The amount of lipase needed will depend on the nature of the reactants, the stoichiometry, the actives content and activity of the particular lipase, the reaction conditions, the desired reaction rate, and other factors within the skilled person's discretion. In general, the amount will be within the range of 0.1 to 20 wt. %, more typically 1 to 15 wt. % or 2 to 10 wt. % based on the amount of unsaturated triglyceride.

The reaction of the unsaturated triglyceride and water or $C_1$-$C_8$ alcohol is performed at a temperature within the range of 20° C. to 80° C., 30° C. to 70° C., or 45° C. to 60° C. A relatively mild temperature is desirable because more elevated temperatures promote migration of acyl groups from the 2-position to a 1- or 3-position from which a fatty acid residue has been removed.

The reaction mixture will comprise a 1,3-dihydroxy-2-monoacylglyceride and fatty esters (if a $C_1$-$C_8$ alcohol is used as the reactant) or fatty acids (if water alone is used as the reactant). The fatty esters or acids will carry through to the next process step. In most of the related art, the 1,3-dihydroxy-2-monoacylglyceride produced at this stage is isolated by column chromatography, liquid extraction, or other means. However, if no action is taken to protect against its occurrence, migration of at least some of the 2-monoacyl product to the more thermodynamically stable 1(3)-product begins and continues until the 1(3)-product predominates. The inventive method overcomes this problem of acyl migration from the 2-position by protecting the 1- and 3-positions.

The lipase is normally removed from the reaction mixture by decantation, filtration, centrifugation, or other similar means when conversion to the 1,3-dihydroxy-2-monoacylglyceride is shown to be reasonably complete by gas chromatography, thin-layer chromatography, or other suitable analytical methods. Any remaining alcohol or water can be left in the liquid mixture at this stage or it can be partially or completely removed by stripping. In some aspects, the lipase and any water or $C_1$-$C_8$ alcohol are removed from the reaction mixture prior to the second step, preferably at a temperature less than 80° C.

B. Preparation of a 2-monoacylglyceride Acetal or Ketal

In a second step of the inventive method, the mixture comprising the 1,3-dihydroxy-2-monoacylglyceride and the fatty esters or acids is reacted with at least one molar equivalent of an aldehyde or ketone, optionally in the presence of an acid catalyst, to produce a mixture comprising the fatty esters or acids and a 2-monoacylglyceride acetal or ketal.

Generally, the reaction of aldehydes or ketones with glycols in the presence of an acid catalyst to form cyclic, 5- or 6-membered ring acetals or ketals is a known way to protect carbonyl groups, although the reaction has apparently not been utilized to protect 1,3-dihydroxy-2-monoacylglycerides. Glycerol has the ability to form either a 5-membered ring (using adjacent hydroxyl groups) or a 6-membered ring (using hydroxyl groups at the 1- and 3-positions). Although glycerol favors forming the 5-membered ring (see, e.g., Piantadosi et al., *J. Am. Chem. Soc.* 80 (1958) 6613), a 1,3-dihydroxy-2-monoacyl glyceride can only form a 6-membered cyclic acetal or ketal.

Although any aldehyde or ketone could be used in theory, readily available, simpler aldehydes and ketones are preferred (e.g., acetaldehyde, butyraldehyde, benzaldehyde, acetone), and food-grade aldehydes and ketones are particularly preferred. Food-grade aldehydes and ketones allow the corresponding acetal or ketal to be supplied "as is" for food products, additives, supplements, and the like. Suitable food-grade aldehydes and ketones include, for example, acetaldehyde, hexanal, octanal, benzaldehyde, cinnamaldehyde, vanillin, ethyl vinyl ketone, 2-furyl methyl ketone, methyl 2-pyrrolyl ketone, watermelon ketone, raspberry ketone, and the like. Especially preferred are benzaldehyde, cinnamaldehyde, and vanillin.

An acid catalyst is preferably used, although one may not be necessary in all cases, particularly when the reaction product also includes one or more fatty acids. When an acid catalyst is included, a mineral acid (e.g., phosphoric acid) or an organic acid (e.g., acetic acid or p-toluenesulfonic acid) is well-suited for this purpose. Solid acid catalysts (e.g., silica-aluminas, organic clays, or sulfonic acid resins such as Amberlyst® resins) could also be used.

The reaction mixture from the second step comprises the fatty esters or acids generated in the first step and a 2-monoacylglyceride acetal or ketal. Removal of the fatty esters or acids is desirable for providing a product having an enriched content of polyunsaturated fatty acid. As was noted earlier, polyunsaturated fats will normally have more unsaturation in the fatty acid residue at the 2-position when compared with that of the 1- and 3-positions. When the only remaining fatty acid residue after reaction with the lipase is at the 2-position, the overall unsaturated fatty acid content can be enhanced. Thus, in some aspects, the proportion of unsaturated fatty acid residues in the 2-monoacylglyceride acetal or ketal will be increased relative to the proportion of unsaturated fatty acid residues in the unsaturated triglyceride.

C. Isolation of a Purified 2-monoacylglyceride Acetal or Ketal

Prior art methodologies used to isolate 1,3-dihydroxy-2-monoacylglycerides (i.e., column chromatography, extraction schemes) are generally impractical for industrial scale processes. The same applies to isolation of 2-monoacylglyceride acetals or ketals. We found that the fatty ester or fatty acid by-products can be conveniently removed as overhead products using distillation or wiped-film evaporation to generate a purified 2-monoacylglyceride acetal or ketal. When wiped-film evaporation is used, it may be desirable to utilize two or more passes of the product through the apparatus to remove a greater proportion of the fatty ester or fatty acid by-products. The equipment and conditions (e.g., temperature, feed rate) used for the distillation or wiped-film evaporation will depend on the particular 2-monoacylglyceride acetal or ketal made, the relative boiling ranges of the fatty esters or acids and the 2-monoacylglyceride acetal or ketal, the required degree of separation, and other factors within the skilled person's discretion.

In some cases, it may be desirable to further purify the 2-monoacylglyceride ketal or acetal isolated as described above by distillation. This allows isolation of a purified 2-monoacylglyceride ketal or acetal from less-volatile impurities. This could be performed using any of a number of suitable techniques, including use of a short-path still, bulb-to-bulb distillation, wiped-film evaporation with a side draw, or similar techniques that allow recovery of the desired 2-monoacylglyceride ketal or acetal as an overhead product.

Although the 2-monoacylglyceride will often be the end product, it may be desirable in some cases to react a purified 2-monoacylglyceride acetal or ketal prepared as described above with water or a $C_1$-$C_8$ alcohol in the presence of a base to produce an enriched unsaturated fatty acid or an enriched $C_1$-$C_8$ alkyl ester of an unsaturated fatty acid. Because these unsaturated fatty acids or esters have unsaturation that originated at the 2-position of an unsaturated triglyceride, usually a polyunsaturated triglyceride, they will often be rich in polyunsaturated content.

II. Preparation and Purification of
1,3-dicarboxy-2-monoacylglycerides

In another aspect, the invention relates to a method of preparing and purifying a 1,3-dicarboxy-2-monoacylglyceride. The method comprises two steps. First, an unsaturated triglyceride is reacted with at least two molar equivalents of a lower alkyl ester or carboxylic acid in the presence of a lipase at a temperature within the range of 20° C. to 80° C. for a time sufficient to produce a reaction mixture comprising a 1,3-dicarboxy-2-monoacylglyceride and fatty esters or acids. Thereafter, the fatty esters or acids from the mixture in the first step are removed as an overhead product by distillation or wiped-film evaporation to isolate a purified 1,3-dicarboxy-2-monoacylglyceride.

A. Preparation of a
1,3-dicarboxy-2-monoacylglyceride

Suitable unsaturated triglycerides for this method have already been described above. The unsaturated triglyceride is reacted with at least two molar equivalents of a lower alkyl ester or carboxylic acid, preferably a lower alkyl ester.

Suitable lower alkyl esters and carboxylic acids have a linear or branched chain of 1 to 10 carbons. The esters are based on linear or branched alcohols having 1 to 8 carbons, preferably 1 to 4 carbons, most preferably methanol or ethanol, especially ethanol. Thus, examples of suitable lower alkyl esters include methyl acetate, ethyl acetate, ethyl lactate, ethyl butyrate, ethyl 2-ethylhexanoate, octyl acetate, and the like. Ethyl acetate is preferred. Examples of suitable lower carboxylic acids include acetic acid, propionic acid, butyric acid, hexanoic acid, octanoic acid, 2-ethylhexanoic acid, decanoic acid, and the like. Acetic acid is preferred.

Suitable lipases have already been described above.

The reaction of unsaturated triglyceride and the lower alkyl ester or carboxylic acid is performed at a temperature within the range of 20° C. to 80° C., 30° C. to 70° C., or 45° C. to 60° C. Although less of a concern in this method, relatively mild temperature is desirable here as well to avoid scrambling of the 2-acyl group to either the 1- or 3-position under the reaction conditions used to form the desired 1,3-dicarboxy-2-monoacylglyceride.

The reaction mixture will comprise a 1,3-dicarboxy-2-monoacylglyceride and fatty esters (if a lower alkyl ester is used as the reactant) or fatty acids (if a lower carboxylic acid is used as the reactant). The fatty esters or acids will carry through to the next process step.

In preferred aspects, the proportion of unsaturated fatty acid residues in the 1,3-dicarboxy-2-monoacylglyceride is increased relative to the proportion of unsaturated fatty acid residues in the unsaturated triglyceride.

The lipase can be removed from the reaction mixture by decantation, filtration, centrifugation, or other similar means when conversion to the 1,3-dicarboxy-2-monoacylglyceride is shown to be reasonably complete by gas chromatography, thin-layer chromatography, or other suitable analytical methods. Any remaining lower alkyl ester or carboxylic acid can be left in the liquid mixture at this stage or it can be partially or completely removed by stripping. In some aspects, lower alkyl ester or carboxylic acid is removed from the reaction mixture prior to the second step, preferably at a temperature less than 80° C.

B. Isolation of a Purified
1,3-dicarboxy-2-monoacylglyceride

While column chromatography and extraction have been used in the past to isolate 1,3-dicarboxy-2-monoacylglycerides, these laboratory solutions are generally impractical for industrial processes. As noted above for the 2-monoacylglyceride acetals or ketals, we found that the fatty ester or fatty acid by-products can be conveniently removed as overhead products using distillation or wiped-film evaporation to generate a purified 1,3-dicarboxy-2-monoacylglyceride. When wiped-film evaporation is used, it may be desirable to utilize two or more passes of the product through the apparatus to remove a greater proportion of the fatty ester or fatty acid by-products. The equipment and conditions (e.g., temperature, feed rate) used for the distillation or wiped-film evaporation will depend on the particular 1,3-dicarboxy-2-monoacyl glyceride made, the relative boiling ranges of the fatty esters or acids and the 1,3-dicarboxy-2-monoacyl glyceride, the required degree of separation, and other factors within the skilled person's discretion.

In some cases, it may be desirable to further purify the 1,3-dicarboxy-2-monoacylglyceride isolated as described above by distillation. This allows isolation of a purified 1,3-dicarboxy-2-monoacylglyceride from less-volatile impurities. This could be performed using any of a number of suitable techniques, including use of a short-path still, bulb-to-bulb distillation, wiped-film evaporation with a side draw, or similar techniques that allow recovery of the desired 1,3-dicarboxy-2-monoacylglyceride as an overhead product.

Although the 2-monoacylglyceride will often be the end product, it may be desirable in some cases to react a purified 1,3-dicarboxy-2-monoacylglyceride prepared as described above with water or a $C_1$-$C_8$ alcohol in the presence of a base to produce an enriched unsaturated fatty acid or an enriched $C_1$-$C_8$ alkyl ester of an unsaturated fatty acid. Because these unsaturated fatty acids or esters have unsaturation that originated at the 2-position of an unsaturated triglyceride, usually a polyunsaturated triglyceride, they will often be rich in polyunsaturated content.

The following examples merely illustrate the invention; those skilled in the art will recognize many variations that are within the spirit of the invention and scope of the claims.

Example 1

Preparation of a 1,3-Diacetyl-2-Monoacylglyceride
from Fish Oil

Fish oil (Nestlé type NAD Hi EPA, 2168.7 g, 2.54 mol), ethyl acetate (6385 g, 72.5 mol), and lipase (Lipozyme® TL IM, product of Novozymes, 166.9 g) are combined and agitated at room temperature for 5 to 10 days, after which time the monoacetyl triglyceride content is less than 15%. The lipase is removed by filtration, and excess ethyl acetate is stripped (45-50° C., 40 mm Hg).

The crude reaction mixture is combined with material from a similar run and is purified by wiped-film evaporation (2" diameter, UIC).

First pass conditions (to remove more-volatile side products): 218° C. (oil), 1.8 mm Hg. The feed (4240 g) is charged over 8 h, and a bottoms stream (2780.2 g) is retained. Second pass conditions: 229° C. (oil), 1.0 mm Hg. The feed (2780.2 g) is charged over 8 h, and a bottoms stream (2101.4 g) is retained.

Product pass conditions (to remove less-volatile side products): Pass 1: 242° C. (oil), 0.40 mm Hg. An overhead fraction (456.7 g) is isolated from a bottoms fraction (1535.7 g). Pass 2: 246° C. (oil), 0.35 mm Hg. An overhead fraction (327.8 g) is isolated from a bottoms fraction (1113.7 g). The overhead fractions from Pass 1 and Pass 2, which comprise the desired 1,3-diacetyl-2-monoacylglyceride product, are combined and analyzed.

Example 2

Preparation of a 2-Monoacylglyceride Acetal from Fish Oil and Vanillin

Fish oil (Nestlé type NAD Hi EPA, 1085.3 g, 1.27 mol), absolute ethanol (2282.0 g, 49.54 mol), and lipase (Lipozyme® TL IM, 277 g) are combined and held at 18-21° C. After gas chromatography analysis shows that the reaction is reasonably complete, the lipase is removed by filtration. Vanillin (132.6 g, 0.872 mol) and phosphoric acid (85% $H_3PO_4$, 3.38 g) are added to the filtrate, and excess ethanol is stripped (35-45° C., pressure gradually reduced to 1 mm Hg over 2.75 h). The reaction temperature is increased to 50° C. to complete the acetal formation. The mixture is cooled, and the vacuum is broken with nitrogen. Aqueous sodium bicarbonate (2.6 g in 25 mL of water) is added to neutralize the acid catalyst.

The crude reaction mixture is combined with material from a similar run and is purified by wiped-film evaporation (2" diameter, UIC).

Two passes, both at 220° C. (oil), 1.0 mm Hg, are used to remove the more-volatile by-products. The feed (about 1800 g) is charged over 1.5 h for the first pass and 0.5 h for the second pass. A combined overhead stream (1278.6 g), primarily residual ethanol and fatty ethyl esters, is separated from the desired 2-monoacylglyceride vanillin acetal (516.3 g).

Example 3

Preparation of a 2-Monoacylglyceride Acetal from Safflower Oil and Benzaldehyde

High-linoleic safflower oil (300 g, 0.343 mol, 81% linoleate content), 1-butanol (600 g), water (33 g), and lipase (Lipozyme® RM IM, product of Novozymes, 3.6 g) are combined under nitrogen and heated to 50° C. After 3.5 h at 50° C., the lipase is removed by filtration. Benzaldehyde (42.0 g, 0.396 mol) and p-toluenesulfonic acid monohydrate, "p-TSA" (2.5 g) are added to the filtrate, and the mixture is heated to 55° C. under reduced pressure (100 to 10 mm Hg). After 2 h, potassium acetate is added to neutralize the p-TSA, and the mixture is filtered. The light-yellow filtrate (366.2 g) is passed through a wiped-film evaporator (179° C. (jacket); 0.04 mm Hg) to remove fatty butyl esters formed as a side product. The desired 2-monoacylglyceride benzaldehyde acetal is recovered on the second and third passes (177-197° C., 0.02 mm Hg). Yield: 70 g; 84% of 2-MAG acetal. Conversion of the 2-MAG acetal to methyl esters results in a product having 91% linoleate content, an increase of 12% compared with the linoleate content of the safflower oil.

Example 4

Preparation of a 2-Monoacylglyceride Acetal from Soybean Oil and Cinnamaldehyde

Soybean oil (20.0 g, 0.0229 mol), 1-octanol (82 g), water (2.2 g), and lipase (Lipozyme® RM IM, 3.6 g) are combined under nitrogen and heated to 60° C. After 5 h at 60° C., the lipase is removed by filtration. Cinnamaldehyde (4.0 g, 0.0303 mol) and p-TSA (0.25 g) are added to the filtrate, and the mixture is heated to 55° C. under reduced pressure (1 to 2 mm Hg). After 3 h, potassium acetate is added to neutralize the p-TSA, and the mixture is filtered. Gas chromatography analysis of the reaction mixture shows formation of the desired 2-monoacylglyceride cinnamaldehyde acetal.

Example 5

Preparation of a 2-Monoacylglyceride Acetal from Menhaden Oil and Cinnamaldehyde Menhaden oil (50.0 g, 0.0586 mol), acetonitrile (132 g), water (2.2 g, 0.122 mol), cinnamaldehyde (11.1 g, 0.102 mol), and lipase (Lipozyme® TL IM, 7.9 g) are combined under nitrogen and heated to 55° C. After 6 h at 60° C., the lipase is removed by filtration. p-Toluenesulfonic acid (0.50 g) is added to the filtrate, and the mixture is heated to 55° C. under reduced pressure (100 to 10 mm Hg). After 2 h, sodium bicarbonate is added to neutralize the p-TSA, and the mixture is filtered. Gas chromatography analysis of the reaction mixture shows formation of the desired 2-monoacylglyceride cinnamaldehyde acetal.

The preceding claims are meant only as illustrations; the following claims define the inventive subject matter.

I claim:

1. A method comprising:
   (a) reacting an unsaturated triglyceride with at least two molar equivalents of water, a $C_1$-$C_8$ alcohol, or a mixture thereof in the presence of a lipase at a temperature within the range of 20° C. to 80° C. for a time sufficient to produce a reaction mixture comprising a 1,3-dihydroxy-2-monoacylglyceride and fatty esters or acids;
   (b) reacting the 1,3-dihydroxy-2-monoacylglyceride with at least one molar equivalent of a food-grade aldehyde or ketone, optionally in the presence of an acid catalyst, to produce a mixture comprising the fatty esters or acids and a 2-monoacylglyceride acetal or ketal;
   (c) removing the fatty esters or acids from the mixture in step (b) as an overhead product by wiped-film evaporation to isolate a purified 2-monoacylglyceride acetal or ketal; and
   (d) further purifying the 2-monoacylglyceride acetal or ketal from step (c) by wiped-film evaporation with a side draw to remove less-volatile impurities and isolate a further purified 2-monoacylglyceride acetal or ketal that is suitable for human consumption.

2. The method of claim 1 wherein the proportion of unsaturated fatty acid residues in the 2-monoacylglyceride acetal or ketal is increased relative to the proportion of unsaturated fatty acid residues in the unsaturated triglyceride.

3. The method of claim 1 wherein the unsaturated triglyceride is an omega-3 fatty acid-rich oil.

4. The method of claim 3 wherein the omega-3 fatty acid-rich oil comprises fatty acid residues of eicosapentaenoic acid (EPA), docosahexaenoic acid (DHA), or both.

5. The method of claim 1 wherein the lipase is a 1,3-position specific lipase.

6. The method of claim 5 wherein the 1,3-position specific lipase is obtained from an organism selected from the group consisting of *Candida antarctica, Candida rugosa, Thermomyces lanuginosus, Rhizopus delemar, Rhizomucor miehei*, and combinations thereof.

7. The method of claim 1 wherein the $C_1$-$C_8$ alcohol is ethanol.

8. The method of claim 1 wherein the reaction in step (a) is performed at a temperature within the range of 45° C. to 60° C.

9. The method of claim 1 wherein the food-grade aldehyde is selected from the group consisting of benzaldehyde, vanillin, and cinnamaldehyde.

10. The method of claim 1 wherein the lipase and any water or $C_1$-$C_8$ alcohol are removed from the reaction mixture prior to step (b), and any water or $C_1$-$C_8$ alcohol is removed at a temperature less than 80° C.

11. The method of claim 1 further comprising reacting the purified 2-monoacylglyceride acetal or ketal from step (d) with water or a $C_1$-$C_8$ alcohol in the presence of a base to produce an enriched unsaturated fatty acid or an enriched $C_1$-$C_8$ alkyl ester of an unsaturated fatty acid.

* * * * *